(12) United States Patent
Steiner

(10) Patent No.: US 11,618,026 B2
(45) Date of Patent: Apr. 4, 2023

(54) FALSE BOTTOM SPECIMEN TRANSPORT TUBE

(71) Applicant: Michelle Nicole Steiner, Bismarck, ND (US)

(72) Inventor: Michelle Nicole Steiner, Bismarck, ND (US)

(*) Notice: Subject to any disclaimer, the term of this patent is extended or adjusted under 35 U.S.C. 154(b) by 37 days.

(21) Appl. No.: 16/513,635

(22) Filed: Jul. 16, 2019

(65) Prior Publication Data

US 2020/0391205 A1 Dec. 17, 2020

Related U.S. Application Data

(60) Provisional application No. 62/819,654, filed on Mar. 17, 2019.

(51) Int. Cl.
*B01L 3/00* (2006.01)
*A61J 1/14* (2023.01)
*G01N 33/80* (2006.01)

(52) U.S. Cl.
CPC ............ *B01L 3/5082* (2013.01); *A61J 1/1412* (2013.01); *B01L 3/502* (2013.01); *B01L 2200/023* (2013.01); *G01N 33/80* (2013.01)

(58) Field of Classification Search
CPC .. B01L 3/5082; B01L 3/502; B01L 2200/023; B01L 2300/0854; B01L 3/5021; B01L 2300/028; B01L 2300/12; A61J 1/1412; G01N 33/80

USPC .......................................................... 422/549
See application file for complete search history.

(56) References Cited

U.S. PATENT DOCUMENTS

| | | | |
|---|---|---|---|
| 3,955,423 A * | 5/1976 | Ohringer | B01D 33/01 73/863.23 |
| 5,924,594 A * | 7/1999 | Kelly | B01L 3/5082 220/737 |
| 2004/0013574 A1* | 1/2004 | Conway | B01L 3/5082 422/400 |
| 2011/0181875 A1* | 7/2011 | Nakahana | B01L 3/5453 356/246 |

OTHER PUBLICATIONS https://www.globescientific.com/media/PDF/Library_PDF/Tubes-Caps-Racks.pdf. Accessed May 19, 2022. (Year: 2018).*
https://www.globescientific.com/gs-products/test-tubes-vials/false-bottom-tubes.html. Accessed May 19, 2022. (Year: 2018).*

* cited by examiner

*Primary Examiner* — Benjamin R Whatley
*Assistant Examiner* — Jacqueline Brazin
(74) *Attorney, Agent, or Firm* — Fargo Patent & Business Law; Thomas Kading

(57) ABSTRACT

A biological false bottom transport tube system includes a top section manufactured from a top section material and a bottom section below an interior floor. The top section material is transparent to both visible and infrared light, the bottom section fits within the bottom of the top section. The bottom section material is not transparent to either visible or infrared light.

16 Claims, 2 Drawing Sheets

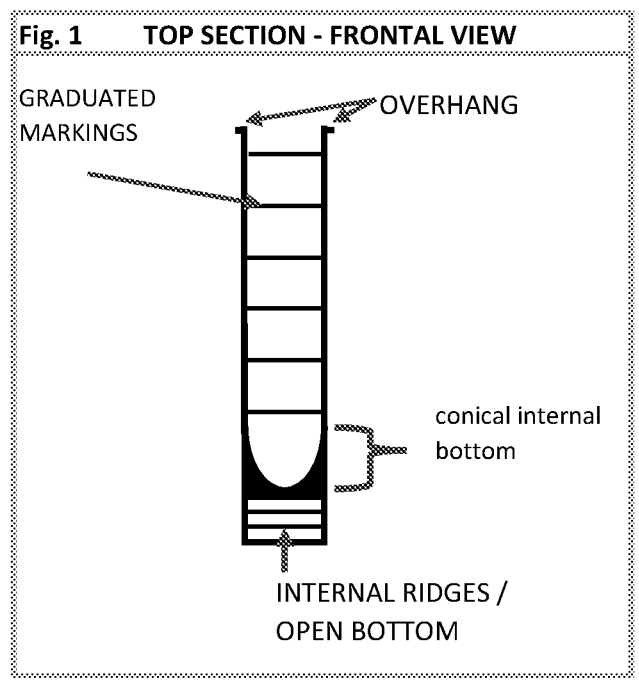

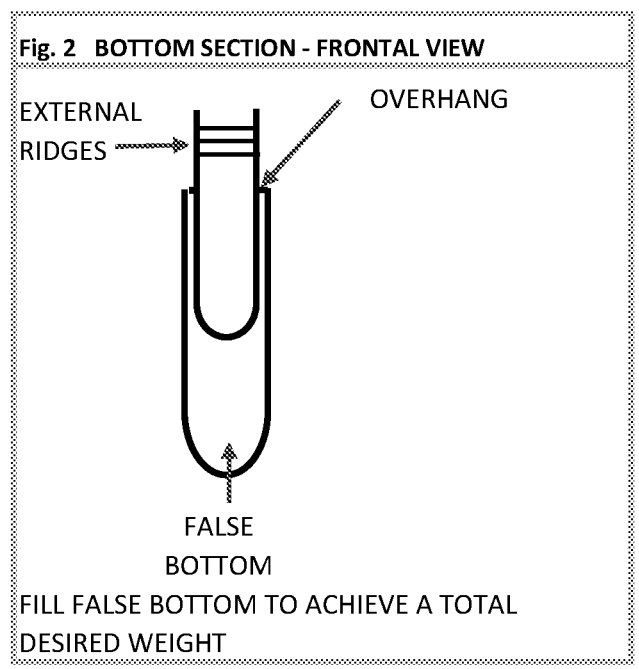

FALSE BOTTOM SPECIMEN TRANSPORT TUBE

CROSS-REFERENCE TO RELATED APPLICATIONS

Appl. No.: U.S. 62/819,654 Filed: Mar. 17, 2019
CPC: A61J 1/1425; B01L 3/14
Field of Search: A61J: 1/1412, 1/1418, 1/1425, 1/1431; B01L 3/14; "test tube".

BACKGROUND

Laboratories often receive biological samples, including serum and plasma, couriered to them from other specimen collection sites. In these cases, the whole blood samples collected at the originating site must be centrifuged, allowing for the separation of the serum/plasma from the red blood cells. The serum/plasma is then removed from the primary collection container and transferred into a specimen transport tube. The specimen is then transported to the testing laboratory. For laboratories that utilize a laboratory automation system, it is essential that the transport tube is compatible with the automation system to ensure efficiency in specimen processing, positive specimen identification, and limitation of potential biological exposure to staff. If the specimen transport tube is not compatible with the automation line, it requires the technologist to revert back to manually processing the specimen, in which case they often have to transfer the specimen into a compatible automation tube. There is also a need for the specimen transport tube to mimic a primary specimen collection tube, to ensure no interruptions in workflow, including creating an imbalance in the centrifuge. This is often accomplished by creating a false bottom, i.e. weighted bottom, which mimics the red blood cell clot in a primary collection container in weight. The transport tube must also allow for the accurate and reliable measurement of specimen in the container by the automation lines sample level detector. Sample level detectors that utilize both visible and infrared light to determine the sample volume in the tube, cannot accurately measure the specimen volume in a typical false bottom transport tube, due to the limitations of the design of the transport tubes on the market today.

SUMMARY

The biological specimen false bottom transport tube will therefore be able to be seamlessly added into normal laboratory workflow, without creating any unbalances during the centrifugation process. A blood specimen containing red blood cells may be taken from a healthy human and such red blood cells taken from a healthy human may become a normal red blood cell clot. The most commonly utilized primary specimen collection tube for medical laboratory samples is a 13 mm×100 mm primary specimen collection tube. Primary specimen collection tubes may come in other sizes and the calculation for the weight of the clot would have to take into account the alternative tube volume for the calculation referenced herein. The estimation of the weight of a clot in a primary collection tube can be calculated with the following known data: tube volume and the hematocrit (HCT) normal range. The HCT test measure the proportion of red blood cells in your blood. The HCT is part of a complete blood count (CBC). The results are reported as the percentage of blood cells that are red blood cells. For example, Mayo Medical Laboratories states that, generally, the combined female and male normal range is 35.5-48.6%. A 13 mm×100 mm collection tube holds 5 mL of whole blood. Therefore, the estimation of the weight of the clot can be determined by the following calculation: Note: 1 mL=1.06 grams, therefore 5 mL of whole blood weighs approximately 5.3 grams.

a. Lower end of range: 0.355×5.3 grams=1.775 mL=1.882 grams b. Upper end of range: 0.486×5.3 grams=2.43 mL=2.576 grams.

DRAWING

FIG. 1 is a front elevation view of a preferred version of the top section of the proposed invention.

FIG. 2 is a front elevation view of a preferred version of the bottom section of the proposed invention.

DESCRIPTION OF THE INVENTION

The invention provides a biological specimen false bottom transport tube that is compatible with laboratory automation systems employing sample level detectors that utilize both visible and infrared light for the determination of sample volume based on the unique spectral properties of serum/plasma, and red blood cells. Since serum/plasma is water based, the absorption characteristics are essentially equivalent to that of water, where red blood cells are significantly opaque to visible light. This allows for the detection of the interface between the serum/plasma and the red blood cell. Both serum/plasma and red blood cells totally absorb infrared light, and therefore the interface between the air and the serum/plasma is only determined by the infrared light. Through the combination of both visible and infrared light, the difference in absorption characteristics allows for the accurate determination of the serum/plasma sample. The describe invention is constructed of a material that is transparent to both visible and infrared light for the top section (FIG. 1), while the bottom section (FIG. 2) is completely opaque to both visible and infrared light. The material is typically, but not necessarily, a soda lime, borosilicate, or Pyrex® glass or a polypropylene, polymethylpentene, polycarbonate, etc. Plastic. The difference in the materials absorption characteristics allows for the accurate determination of sample volume with sample level detectors using both visible and infrared light. Referring to FIG. 2, bottom section, the material used may be amended with additional additives to achieve the desired weight. The entire weight of both the top section (FIG. 1) and the bottom section (FIG. 2), along with the specimen cap, will mimic the weight of a primary specimen collection container. The proposed invention will therefore be able to be seamlessly added into normal laboratory workflow, without creating any unbalances during the centrifugation process.

Although the present invention has been described in considerable detail, with reference to preferred version thereof, other versions are possible based on various manufacturing options. For example, the bottom section (FIG. 2) may have a dye or coloring added during the manufacturing process to indicate what type of sample is being sent. Commonly utilized color coding of specimen collection tubes are listed:

| Color: | Additive in the Specimen: |
| --- | --- |
| Red | SST/Serum |
| Green | PST/Heparin Plasma |
| Purple | EDTA Plasma |
| Blue/White | Citrate Plasma |

The present invention may also use the above coding, or still other color coding may be used. It should be noted that "color" is intended to refer broadly to visually distinguishable characteristics, and includes not only the specific colors of the light spectrum but also such colors with textures and/or designs in the appearance. Graduation markings may be added during the manufacturing process at specific intervals to allow for accurate estimation of sample volume. Each feature disclosed in the specification, include the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A biological false bottom transport tube system comprising:
a top section of a 13 mm×100 mm specimen tube body, the top section comprising a top, an interior floor, and a bottom, wherein the top section is manufactured from a top section material, wherein the bottom is below the interior floor, wherein the bottom is open, the bottom further comprising an internal ridge, wherein the top section material is transparent to both visible and infrared light, wherein the top section may hold a sample; and
a bottom section of the 13 mm×100 mm specimen tube body, the bottom section comprises a top of the bottom section and a bottom section weight, wherein the bottom section is manufactured from a bottom section material, the top of the bottom section less than 13 mm in diameter to fit within the bottom of the top section, the top of the bottom section comprising an external ridge, wherein the external ridge is configured to secure at least partially into the internal ridge in the bottom of the top section such that the top of the bottom section is secured within the bottom of the top section, wherein the bottom section material is not transparent to either visible or infrared light, wherein the bottom section weight is between 1.882-2.576 grams.

2. The biological false bottom transport tube system of claim 1, wherein the interior floor is of a semi-spherical shape.

3. The biological false bottom transport tube system of claim 1, wherein the sample is serum or plasma.

4. The biological false bottom transport tube system of claim 1, further comprising a graduated marking on the top section.

5. The biological false bottom transport tube system of claim 4, wherein the bottom section is color coded.

6. The biological false bottom transport tube system of claim 1, wherein the sample is a biological specimen.

7. A biological false bottom transport tube system comprising:
a top section of a 13 mm×100 mm specimen tube body, the top section comprising a top, an interior floor, a graduated marking, and a bottom, wherein the top section is manufactured from a top section material, wherein the bottom is below the interior floor, wherein the bottom is open, the bottom further comprising an internal ridge, wherein the top section material is transparent to both visible and infrared light, wherein the top section may hold a sample, wherein the sample is serum or plasma, wherein the sample is a biological specimen, wherein the interior floor is a semi-spherical shape; and
a bottom section of the 13 mm×100 mm specimen tube body, the bottom section comprises a top of the bottom section and a bottom section weight, wherein the bottom section is manufactured from a bottom section material, the top of the bottom section less than 13 mm in diameter to fit within the bottom of the top section, the top of the bottom section comprising an external ridge, wherein the external ridge is configured to secure at least partially into the internal ridge in the bottom of the top section such that the top of the bottom section is secured within the bottom of the top section, wherein the bottom section material is not transparent to either visible or infrared light, wherein the bottom section weight is equivalent to a blood clot weight of a combined female and male hematocrit normal range of 35.5-48.6%, that contains 5 mL of whole blood, wherein the bottom section is color coded.

8. The biological false bottom transport tube system of claim 1, wherein the bottom section is color coded.

9. The biological false bottom transport tube system of claim 1, wherein the bottom section material is red in color.

10. The biological false bottom transport tube system of claim 1, wherein the bottom section material is green in color.

11. The biological false bottom transport tube system of claim 1, wherein the bottom section material is purple in color.

12. The biological false bottom transport tube system of claim 1, wherein the bottom section material is blue in color.

13. The biological false bottom transport tube system of claim 7, wherein the bottom section material is color coded red in color.

14. The biological false bottom transport tube system of claim 7, wherein the bottom section material is color coded green in color.

15. The biological false bottom transport tube system of claim 7, wherein the bottom section material is color coded purple in color.

16. The biological false bottom transport tube system of claim 7, wherein the bottom section material is color coded blue in color.

* * * * *